United States Patent
Michel et al.

(10) Patent No.: US 11,506,591 B2
(45) Date of Patent: Nov. 22, 2022

(54) SYSTEM AND METHOD OF USE FOR ELECTRICALLY DIFFERENTIATING PARTICLES IN A LIQUID

(71) Applicant: Woods Hole Oceanographic Institution, Woods Hole, MA (US)

(72) Inventors: Anna Pauline Miranda Michel, Falmouth, MA (US); Beckett Colson, Falmouth, MA (US)

(73) Assignee: Woods Hole Oceanographic Institution, Woods Hole, MA (US)

(*) Notice: Subject to any disclaimer, the term of this patent is extended or adjusted under 35 U.S.C. 154(b) by 218 days.

(21) Appl. No.: 17/018,626

(22) Filed: Sep. 11, 2020

(65) Prior Publication Data

US 2021/0072137 A1 Mar. 11, 2021

Related U.S. Application Data

(60) Provisional application No. 63/076,686, filed on Sep. 10, 2020, provisional application No. 62/977,695, filed on Feb. 17, 2020, provisional application No. 62/898,747, filed on Sep. 11, 2019.

(51) Int. Cl.
*G01N 15/10* (2006.01)
*G01N 33/44* (2006.01)

(52) U.S. Cl.
CPC ....... *G01N 15/1031* (2013.01); *G01N 33/442* (2013.01); *G01N 2015/1081* (2013.01)

(58) Field of Classification Search
CPC .. B07C 5/344; G01N 15/1031; G01N 33/442; G01N 2015/1081
See application file for complete search history.

(56) References Cited

U.S. PATENT DOCUMENTS

| | | | | |
|---|---|---|---|---|
| 2003/0175980 | A1* | 9/2003 | Hayenga | B07C 5/342 436/63 |
| 2009/0148937 | A1* | 6/2009 | Schnelle | B01L 3/502753 209/132 |
| 2014/0261757 | A1* | 9/2014 | Katsumoto | G01N 15/1404 137/268 |
| 2022/0034781 | A1* | 2/2022 | Morgan | C12Q 1/18 |
| 2022/0050031 | A1* | 2/2022 | Anand | A61M 1/1603 |

* cited by examiner

*Primary Examiner* — Joseph C Rodriguez
(74) *Attorney, Agent, or Firm* — Kean Miller LLP; Robert Devin Ricci; Brian J. Serve (57) ABSTRACT

A system for the differentiation of plastic and non-plastic particles in suspension in a liquid, and the method of use thereof. The system having a channel for constraining and presenting the liquid to a detector, the detector having at least one transmit electrode for emitting electrical current to at least one receive electrode. Circuitry provides the current input and received electrical signals measurement capacities. Particles passing the receive electrodes alter the received electrical current according to the particle's dielectric properties, the circuitry records the received signals and discerns a particle's nature, most often plastic from non-plastic, from the differential signal of these received signals as a function of frequency.

15 Claims, 5 Drawing Sheets

SYSTEM AND METHOD OF USE FOR ELECTRICALLY DIFFERENTIATING PARTICLES IN A LIQUID

CROSS-REFERENCE TO RELATED APPLICATIONS

This application claims priority to U.S. Provisional Applications Nos. 62/898,747 filed Sep. 11, 2019, 62/977,695 filed Feb. 17 2020, and 63/076,686 Sep. 10, 2020, the contents of which are all hereby incorporated as if set forth herein in its entirety.

FIELD OF THE INVENTION

This invention relates to methods for the identification of parameters associated with suspended particles, more specifically this invention relates to electrical impedance spectroscopy systems and methods of use, for the detection and characterization of particles, particularly plastic substances and polymers and the differentiation of those particles from organic materials.

BACKGROUND OF THE INVENTION

A common problem is the contamination of an environment with plastic wastes, and the identification of said contamination. Plastics are materials comprising a wide range of molecular compounds, either naturally occurring, synthetically produced or a combination thereof. Plastics are malleable and can be molded into solid objects. Plastics are typically organic polymers with high molecular mass combined with other molecules, or plasticizers that give the solid object its desired properties. Plastic waste breaks down in the environment when exposed to harsh conditions, for example sun-light and repeated motion (e.g. breaking ocean waves).

Consistent, objective, and quantitative methods are needed to understand the fate and effects of plastic wastes in aquatic environments. Manual identification of individual particles is time-consuming and expensive, and lab instrumentation is required for further identifying polymer types.

Plastic is the most prevalent type of waste found in marine environments (e.g. the ocean) and is present a wide range of sizes. Plastic less than five millimeters in its longest dimension is commonly referred to as microplastics. Due to their small size, microplastics present potential health risks from ingestion and other routes of entry to humans as well as marine life.

It is therefore desirable to at least identify and characterize microplastics from an environment of interest. In addition, the removal of microplastics is also desirable. The identification of small molecules, microplastics included, has be performed with many different methods. One method currently unused however, is electrical impedance spectroscopy. Impedance spectroscopy offers a method to identify particles by their dielectric properties in situ, without the need for filtration. Impedance refers to the frequency dependent resistance to current flow of a circuit element (i.e. a resistor, capacitor, inductor, and the like). Impedance assumes an electric current of a specific frequency or frequencies (in Hertz or cycles per second) is applied to the circuit (also referred herein as excitation signals). A lack of impedance results in no modification to the received signals, while impedance by a particle changes the received signal from what was originally emitted as the excitation signal. Impedance relates the current passing through a circuit element to the change in magnitude and phase of a voltage signal via Ohm's Law, as shown in Math 1; where I is the current through a conductor between two points, in units of amperes, V is the voltage measured across the conductor in units of volts, and R is the resistance of the conductor, in units of ohms.

$$I = \frac{V}{R} \quad \text{[Math 1]}$$

Often, electrical impedance is measured by applying an AC potential to an electrical cell (often called a flow cell) and measuring the current through the cell. Impedance changes according to the interfering particles' properties (e.g. conductivity). Impedance has two components, imaginary and real impedance. The imaginary component provides a measure of the reactive part of impedance that comes from the circuit's capacitance, while the real component comes from the circuit's resistance. Impedance is the vector sum of the imaginary and real components of the circuit. The impedance can be thought of as the sum of two vectors (imaginary and real) combined. The angle between the two vectors is the phase angle, which changes across different frequencies. Disclosed herein is an inventive electrical impedance spectroscopy system aimed, in part, at plastic particle detection, characterization, and removal from a liquid environment and method of using same.

SUMMARY OF THE INVENTION

An object of the present invention is a device for the detection of particles suspended in a liquid. The device having a channel for accepting and constraining a working fluid. The channel enables particles suspended in the working fluid to pass between transmit and receive electrodes situated on opposing sides of the channel wall. The two electrodes are most often opposite each other and the transmit electrode emits excitation signals at at least one frequency into the channel. The receive electrode detects the excitation signals, which would have been affected by a particle, if one passed between the two electrodes. The device further has circuitry that connects to both the transmit and receive electrodes, supplies upstream current to the transmit electrode, and receives first downstream current from the receive electrode The circuitry then measures the impedance of the working fluid using the downstream current and determines if a particle was present between the transmit and receive electrodes and also determines at least one parameter of the passing particle. Most often, the at least one parameter is whether the particle is a plastic substance or not.

In some embodiments, the device further differentiates particles between a plastic substance and an organic substance (i.e. organic material), where organic relates to living or once recently alive materials. In some embodiments, the circuitry differentiates particles between plastic substances, organisms and seeds. In some embodiments, the transmit electrode emits a second frequency into the channel, the receive electrode receives the second frequency, and incorporates that information into the downstream currents. In some of these embodiments, circuitry differentiates particle nature by comparing particle peak height at the first frequency vs the second frequency (as graphically illustrated in FIGS. 7E-G). In some embodiments the device is further connected to a controller and in some of these embodiments, the controller has a display feature configured to display particles graphed by the first frequency and the second frequency peak heights. In some of these cases a user pre-defines bounding areas of the graphed particles (by first and second frequency peak height). In other cases, the controller dynamically assigns bounding blocks or classifications based on measured particles and groupings.

In some embodiments, the transmit electrode emits a plurality of frequencies, the receive electrode receives the plurality of frequencies and incorporates the information into the downstream currents. The circuitry may then compare particle peak heights from the first frequency of the plurality of frequencies to a second frequency of the plurality of frequencies. In some cases, the circuitry compares many frequency pairs from the plurality of frequencies and in additional cases modifies which pairs of frequencies are used based on gap analysis from previous picked frequency pairs.

In some embodiments, the device has a filter to prevent a portion of suspended particles from entering the channel. In some cases, the filter prevents particles greater than 1 cm from entering. In other cases, the filter prevents particles of greater than 5 mm from entering. In other cases, the filter prevents particles of greater than 1 mm from entering the channel; in still others, particles greater than 500 micrometers.

Another object of the invention is for the device to have more than one receive electrode. In one embodiment, a second receive electrode is connected to the circuitry, in contact with the channel and on the channel opposite the transmit electrode. The second receive electrode also receives the excitation signals and converts them to second downstream current; and in some cases, circuitry utilizes the second downstream current to calculate peak height and impedance of a passing particle. In some embodiments, the device further includes a first guard electrode that receives the excitation signals, and in some cases the first guard electrode is connected to circuitry; in some cases the first guard electrode produces third downstream current, and in still other cases, the first guard electrode is not connected to circuitry but connected to ground In some cases the guard electrode is connected to a star ground. In some cases, the first guard electrode has a fixed potential.

In some embodiments, the device has a total of two guard electrodes (referred herein as the first and the second guard electrodes). These first and second guard electrodes may be connected to the device as described for the first guard electrode above. In some embodiments the device has a total of three guard electrodes, having a third guard electrode beyond the first and second guard electrodes; the third guard electrode is connected as described above for the first guard electrode. In some embodiments at least two guard electrodes are positioned on opposite sides of the first receive electrode, along the channel wall. In some cases, the channel is elongated and the at least two guard electrodes are positioned on opposite sides of the first receive electrode along the elongated wall or axis of the elongated channel wall.

Figure 7A:
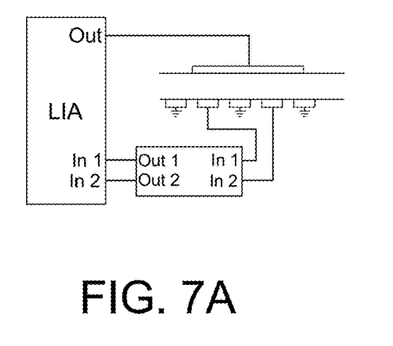
FIGS. 7A-7G illustrate the arrangement and operation of one embodiment of the present invention.

In embodiments having a first and a second receive electrode and three guard electrodes, the guard electrodes are interspersed between the first and second electrode, that is they are positioned along the channel wall in the order of first guard electrode, first receive electrode, second guard electrode, second receive electrode, and third guard electrode, as illustrated in FIG. 7A.

It is within the scope of the present invention for the device to further have a reference mechanism, the reference mechanism having a reference container that accepts and restrains a reference liquid, a reference transmit electrode and a reference receive electrode. Both reference electrodes are connected to the circuitry, and the reference transmit electrode receives upstream current from the circuitry and emits reference excitation signals into the reference liquid. The reference receive electrode receives the reference excitation signals and sends downstream current to the circuitry. In some embodiments the working fluid moves through the channel.

This invention also provides a method of measuring the impedance of suspended particles in a liquid, the method including the following steps of selecting a device; the device having a channel, a transmit electrode, a first receive electrode and circuitry and wherein all the components are connected as described above; supplying a working fluid to the channel of the device; emitting excitation signals from the transmit electrode into the working fluid; receiving the excitation signals by the receive electrode; producing first downstream current; sending the first downstream current to the circuitry, measuring at least one of the following group of the impedance, resistance, or capacitance of the working fluid; and determining at least one parameter of the particle suspending in the working fluid.

In some methods, the at least one parameter is whether the particle is a plastic substance or not. In some methods the at least one parameter is whether the particle is a plastic substance, an organic substance, or an organism. In some methods the device includes additional electrodes, for example a second receive electrode. Another example is a first guard electrode or a first, second or third guard electrode. These additional electrodes are connected to the device as described above.

Some methods include the step of moving the working fluid through the channel. Some methods further include the step of connecting a diverter to the device's channel, and in some cases, the step of connecting a clean-up mechanism to the diverter, and diverting particles determined to be plastic substances (by the circuitry) to the clean-up mechanism. Some methods include the step of connecting an identification system to the device's channel and identifying the chemical composition of particles flowing through the device. Some of these methods includes the step of connecting a diverter and clean-up mechanism and the step of diverting identified plastic particles to the clean-up mechanism. Still other methods includes the steps of connecting a diverter to the device's channel and connecting an identification system to the diverter, diverting plastic substance particles (as determined by circuitry) to the identification system, and identifying the chemical composition of particles in the identification system.

BRIEF DESCRIPTION OF THE DRAWINGS

In what follows, preferred embodiments of the invention are explained in more detail with reference to the drawings, in which:

FIGS. 10A and 10B illustrate the differentiation of different particle types by plotting the change in magnitude of the baseline impedance of two frequencies. FIG. 10A illustrates particles having large amplitude changes and FIG. 10B illustrates particles having small amplitude changes.

DEFINITIONS

For the purpose of this disclosure, the term "channel" refers to a mechanism configured to constrain a liquid. The term channel may refer herein as its commonly known definition of a passage, often tubular, for conducting liquid, but may also refer to any vessel or other mechanism that holds a liquid, for example a bottle, a microfluidic channel or a stream of liquid that has been shaped by a force (i.e. hydrodynamic or acoustic focusing).

The term "microplastics" refers herein to plastic particles less than or approximately equal to 5 millimeters in their longest dimension.

The terms "electrical signals" and "excitation signals" refers to electrical field lines of force between a transmit electrode and a receive electrode. A single transmit electrode may produce electrical signals for multiple receive electrodes, each electrical signal may be produced at a multiple frequencies, often a high frequency and a low frequency.

The energy received by a receive electrode after the excitation signals are emitted into the channel is referred herein as the "received signal". The term "particles" is defined for the purpose of this disclosure as a small amount of matter, and can encompass intact objects (e.g. microscopic organisms) or a portion of an object (e.g. a fragment of plastic). The term "particles" further includes both microscopic and macroscopic amounts of matter, for example, depending on the scale of the embodiment of the present invention, a particle of plastic may be a 5 mm sized plastic fragment, or a one inch fragment.

DETAILED DESCRIPTION OF THE PRESENTLY PREFERRED EMBODIMENTS

Overview

In its simplest iteration, this invention may be accomplished by providing circuitry 130 having at least one transmit electrode 111 and a first receive electrode 112, each electrode in contact with, and separated by a channel 102. Channel 102 is designed to hold or pass a working fluid 104 with suspending particles 108 between transmit 111 and receive electrodes 112. Transmit electrode 111 transmits excitation signals 113 with at least one frequency F into the working fluid 104 and receive electrode 112 detects signals 113. Particles passing though signals 113 change the capacitance and resistance between the two electrodes as a function of frequency, and circuitry 130 measures these changes, as the impedance spectrum or the change in resistance amplitude and phase over the one or more frequencies transmitted.

Interconnected circuitry 130 and in some embodiments, an interconnected controller 131 receives the impedance measurements. A slowly varying baseline signal is extracted from the raw data for both real and imaginary impedance. This extracted baseline is used to compute the change in real impedance, change in imaginary impedance and change in impedance magnitude. The change in impedance magnitude is then used to identify peak and valley locations, which may then be used to determine a particle's parameters (e.g. plastic or not plastic).

Figure 2A:
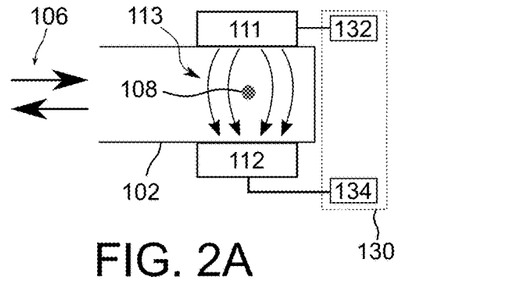
FIGS. 2A-2C are schematic representations of the detector and circuitry according to three embodiments.

A partial illustration of one embodiment is illustrated in FIG. 2A, particles 108 in suspension of a working fluid 104 are introduced to system 100. System 100 comprises channel 102, transmit electrode 111, and receive electrode 112b. Excitation signals 113b are passed from the transmit electrode 111 to the receive electrode 112b. Particles 108 traveling through channel 102 move through the path of the excitation signals 113b, causing a change in the signals, which is then received by the receive electrodes 112b and monitored by circuitry 130, depicted as a dotted box in FIG. 2A. Different individual particles 108 affect the excitation signals 113 in different ways, the system 100 is enabled to discern these differences, thereby informing a user to the particles' parameters or composition. The system 100 typically determines a particle's composition grouped into two groups as either (i) a particle made up of plastic substances (i.e. plastic polymers and plasticizers) or (ii) a particle made up of organic substances or materials (i.e. a binary plastic or not plastic differentiation). To visually differentiate the excitation signals 113, four parallel lines represent signals 113 unaffected by a particle 108 (e.g. excitation signals 113a, and 113c-e in FIG. 2B) or four curving arrows represent signals 113 affected by a passing particle (e.g. excitation signals 113b in FIG. 2B).

Figure 1:
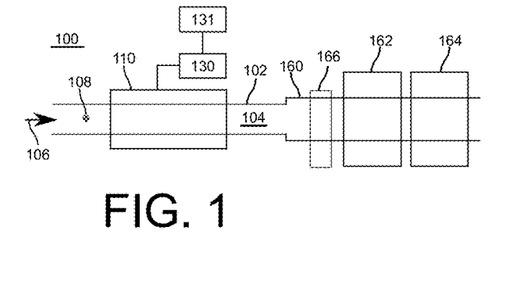
FIG. 1 is a high-level diagram of the device disclosed, according to one embodiment of the present invention.
Figure 2B:
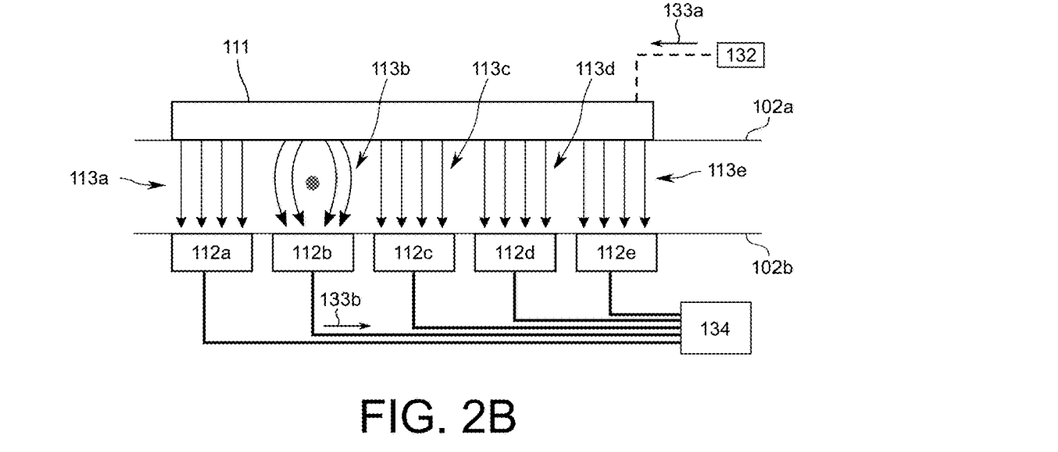

The current invention will now be described according to several different embodiments. The currently preferred embodiment is illustrated in FIGS. 1-2B, comprising system 100 having a flow path 106 of working fluid 104 though channel 102 that travels pasta detector 110 where the impedance of a particle 108 may be measured over a single frequency F or spectrum of frequencies Fn. In such a flow-through embodiment illustrated in FIGS. 1 and 2B, suspended particles 108 passing the electrodes impact the electric field of excitation signals 113, and therefore the effective impedance, according to the particle's unique dielectric properties. The dielectric properties of materials vary based on their physical attributes. By observing changes in impedance at several key frequencies Fn, passing particles can be identified as plastics or non-plastics, or as plastic or a specific type or classification of organic materials.

Channel 102

The present invention is directed towards the detection and measurement of particles 108 suspended in a working fluid 104. Channel 102 is a mechanism enabling the presentation of particles 108 to the detector 110. Typically, channel 102 is a flow-through or in-line structure, a restrictive passage enabling working fluid 104 to move past detector 110. In less preferred embodiments, channel comprises a stationary system (e.g. a sample bottle, a test-tube, or a well plate) which is filled with working fluid 104 by a user or automated mechanism, as illustrated in FIG. 2A. In these stationary flow embodiments, the transmit 111 and receive 112 electrodes may be inserted into the channel 102 or attached at a suitable section of channel 102 wall or opening (i.e. as part of a bottle cap). For the purpose of this disclosure, all surfaces including removable ones (i.e. a bottle cap) are referred herein as walls.

Channel 102 constrains the working fluid 104, typically by providing a physical barrier (e.g. channel walls 102a and 102b). In some less preferred embodiments, working fluid 104 constraint may be achieved by electromagnetic or acoustic methods. Other embodiments may utilize both physical and electromagnetic constraint. Channel 102 most often is described as having two walls 102a and 102b. The channel 102 may be any suitable structure as known in the art, and is often a cylindrical tube. Wall 102a and wall 102b may be different sides of a cylindrical tube and not are not necessarily two distinct structures. Most often wall 102a is directly opposite wall 102b as depicted in FIG. 2B.

Typically, channel 102 contains a moving working fluid 104, the working fluid 104 having a velocity, or flow. Typical flow speeds are with substantially within one thousandths of a liter per minute (1/1000 L/min) to one liter per minute (1 L/min). Preferably, the flow is fast enough to overcome particle buoyancy or particle sinking. Buoyant particles may not properly pass detector 110, or be in an undesirable location in the channel (i.e. immediately proximate an electrode). Particles that sink have similar, but opposite problems as buoyant particles. Channel 102 may be manufactured with any suitable material as known in the art; suitable materials preferably are non-corrosive, non-conductive, and liquid-tight, for example Teflon, or silicone-based materials.

Different embodiments of the present invention may be configured to detect plastic particles of differing sizes. Accordingly, channel 102 may be constructed in different sizes and shapes to accommodate the embodiment. In the currently preferred embodiment, channel 102 is approximately cylindrical with a diameter of 1 cm. In another embodiment, channel 102 is a tube with a diameter of 10 cm. In yet another embodiment, channel 102 is an 8 inch diameter pipe in-line with a wastewater effluent channel. The present invention does not require a filter to remove larger particles or objects from entering channel 102 and most embodiments will not contain a filter. However, some larger embodiments (e.g. an 8 inch diameter channel) may include an optional filter to block large particles or other debris from entering the channel.

Working Fluid 104

System 100 is suited to detect particles 108 in a wide range of liquids, referred herein as working fluid 104. In the currently preferred embodiment, working fluid 104 comprises a water-based liquid; for example freshwater, tap water, or saltwater. Some examples of liquids include potable drinking water, grey water, sea-water, liquids in sewers, raw wastewater influent, wastewater effluent, industrial processing fluids, and the like. Furthermore, it is within the scope of this invention for other liquids to be processed or otherwise used with system 100, for example petrochemical liquids like crude oil, rendered conductive in a pressurized cell. Working fluids 104 having different conductive properties may all be processed by the inventive system described herein.

Typically, the working fluid 104 is introduced to channel 102 without any modifications. However, it is within the scope of the invention for channel 102 to be proceeded by modification mechanism before working fluid 104 enters channel 102. The modification mechanism may be any suitable mechanism as known in the art. Examples of modification mechanism include a filter, a dye injector, an acidification mechanism, a gas exchanger, and the like.

Particles 108

The system 100 disclosed herein discerns between at least two types of particles. The currently preferred embodiment detects differences between plastic and non-plastic particles. The system 100 can be configured to detect any type and size of plastic, with alterations to physical dimensions of system 100, its components and power provided to and by circuitry 130. Types of discernible plastic include, but are not limited to, spherical polyethylene particles, shaved, abraded or otherwise degraded polyvinyl chloride (PVC) particles, polyethylene terephthalate (PET) particles, and the like. Non-plastic particles discernible by system 100 include any conductive or partially conductive particles. Examples include cells, intact organism, seeds, plant matter, and the like. See the Examples Section below herein for description of additional non-plastic particles.

Detector 110

The detector 110 is illustrated in at least FIGS. 2A and 2B, and comprises at least one transmit electrode 111, and at least a first receive electrode 112b. The simplest arrangement is illustrated in FIG. 2A, having an only a first receive electrode 112b. FIG. 2B illustrates a more complex and robust assembly having a plurality of receive electrodes 112a-e with electrodes grouped into guard electrodes 112a, 112c and 112e and measurement electrodes 112b and 112d. Guard electrodes have a fixed potential, provide a uniform field within a channel, improve noise immunity (reducing outside electrical interference), and reduce fringing effects. Guard electrodes may be connected to downstream electronics 134 (see FIG. 2B) or directly to ground (see FIG. 7A). Measurement electrodes detect the change in excitation signals 113 as a particle 108 passes through the detector 110. FIG. 2B is one design of a potential detector, it is to be understood as not to be limiting and that many other electrode designations and arrangements are possible.

In another embodiment, detector 110 has no electrodes configured to be guard electrode, and instead relies on a non-uniform electrical field (i.e. excitation signals 113) as disclosed in U.S. Patent Application US2016/0041081A1, incorporated herein in its entirety by reference.

Figure 4A:
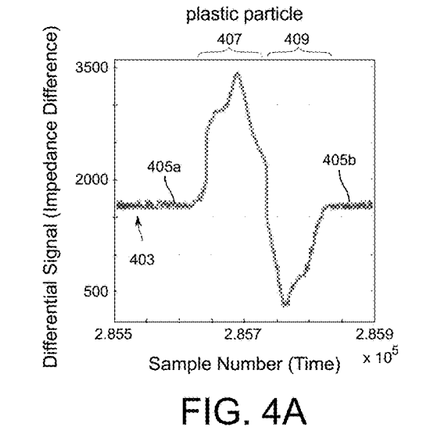
FIGS. 4A and 4B are two representative impedance differential measurements of two different particles measured by one embodiment; a plastic particle is measured in FIG. 4A and a non-plastic, organic particle is measured in FIG. 4B.
Figure 4B:
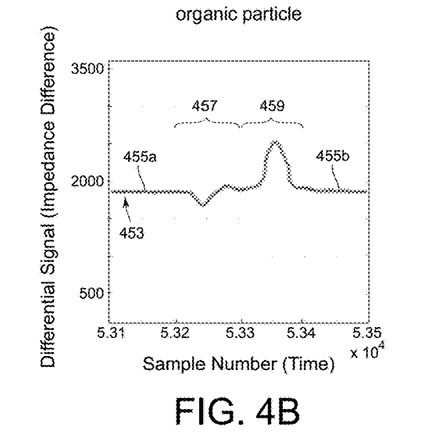

In the currently preferred embodiment, illustrated in FIG. 2B, two measurement receive electrodes 112b and 112d are used as a pair to measure excitation signals 113b and 113d as particle 108 first passes electrode 112b and then electrode 112d. While particle 108 is adjacent (i.e. passing) electrode 112b, that electrode acts as the measurement electrode and electrode 112d acts as a reference electrode (both producing downstream current for the circuitry 130 to assess). Here the reference is where no particle is preferably passing between transmit electrode 111 and receive electrode 112d. Measurement and reference electrode will switch as particle 108 passes receive electrode 112d. The difference between measurement and reference is taken, as a function of time, as particle 108 travels through the detector 110, producing a differential signal, and producing a positive and a negative peak, as illustrated in FIGS. 4A and 4B.

Figure 3:
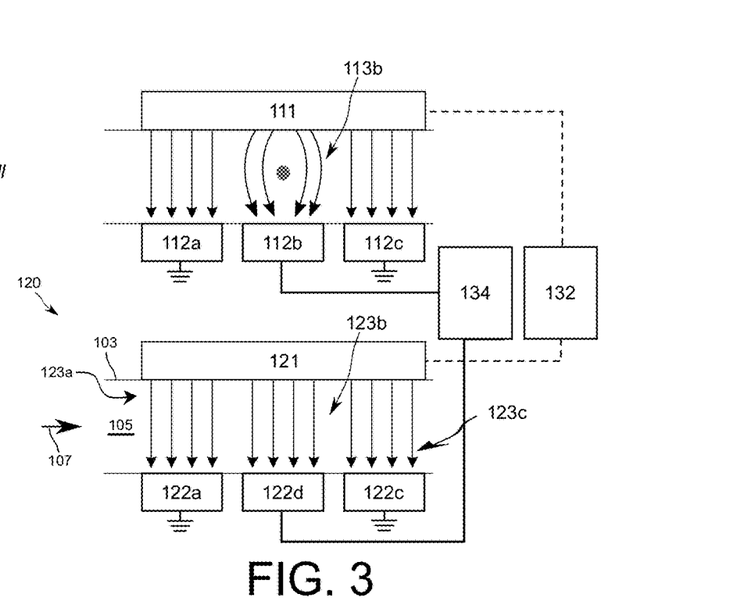
FIG. 3 is a schematic representation of the detector and reference mechanism, according to one embodiment.

In the currently preferred embodiment reference electrode 112d is within the same flow path 106 as measurement electrode 112b, however in other embodiments, reference electrode 112d is in a separate flow path, referred herein as reference path 107, incorporated into a reference mechanism 120, as illustrated in FIG. 3. A reference path 107 would flow a known, often standardized reference liquid 105 past the reference transmit electrode 121 and reference receive electrode 122, eliminating any potential contaminates that could be found in working fluid 104. The reference mechanism 120 may further include guard electrodes 122a and 122c in a similar fashion as described above for guard electrodes 112a and 112c, for example. A system utilizing a single flow path 106 for all electrodes enables the system to easily accommodate changes in working fluid 104 parameters, for example a liquid's conductivity (i.e. salinity) as seen in complex water samples.

A separate reference mechanism 120, illustrated in FIG. 3, comprises a separate reference container 103 (i.e. a second channel) constraining a reference liquid 105, a reference transmit electrode 121 in contact with the reference liquid 105, and a reference receive electrode 122 that is also in contact with the reference liquid 105. The upstream electronics 132 is connected to the reference transmit electrode 121 and downstream electronics 134 is connected to reference receive electrode 122. Reference transmit electrode 121 emits reference excitation signals 123 into the reference container 103. Reference transmit and receive electrodes are positioned on opposing sides of the reference container 103, such that reference excitation signals 123 are emitted from reference transmit electrode 121 (step 608 in FIG. 6B), and received by the reference receive electrode 122. Similar to the detector's excitation signals 113, reference excitation signals 123 are affected by the reference liquid 107 and transformed into reference output signals 124 (step 610), and the reference receive electrodes 122 detect the reference output signals (step 612). The downstream electronics 134 receive the downstream commands of the reference output signals (step 613b) and the interconnected circuitry 130 determines the impedance by the affected signals 114 of particle 108 at measurement electrode 112b minus the reference output signals 124.

Excitation Signals 113

Excitation signals 113, most often having a known AC potential, are emitted into the working fluid 104 in the channel 102 by the transmit electrode 111 and detected or received by the receive electrode 112. The properties of the excitation signals 113 are influenced by any particles 108 in the path of said signals. Excitation signals 113 affected by a particle 108 and as received by the receive electrode 112 are referred herein as affected signals 114. Excitation signals have known properties (e.g. amplitude and phase). Affected signals 114 are the excitation signals 113 as received—by the receive electrode 112. Output signals may be affected by a passing particle 108 and may have changed properties as compared to the known excitation signals 113.

In the currently preferred embodiment, transmit electrode 111 is configured to send excitation signals 113 at a plurality of frequencies F. To enable particle differentiation, transmit electrode 111 must send excitation signals 113 at least one frequency F. In many embodiments, excitation signals 113 are produced at a first, high frequency F1 and at a second, low frequency F2. Typically, low frequencies inform the system of particle 108 size and high frequencies inform the system of particle 108 dielectric properties. The change in the real impedance at low frequency should be proportional to particle volume. Therefore, the cube root of the real impedance change should be proportional to approximate spherical diameter (or equivalent spherical diameter, abbreviated ESD). To obtain a conversion factor needed to change between impedance measurements and the microplastic approximate spherical diameter, a line was fit between the particle 108 diameter and the cube root of the change in real impedance at 10 kHz. In some cases, outliers may be removed. The calculation of ESD is given in Math 2, where a is the conversion factor and $\Delta \text{Re}(\tilde{Z})$ is the measurement of the change in real impedance at 10 kHz. The conversion factor was applied to the particle detections to compare the measured size distribution to the diameter range specified by the manufacturer for each bead size $$ESD = a\sqrt[3]{\Delta \text{Re}(\tilde{Z})} \qquad \text{[Math 2]}$$

In one embodiment, the first frequency F1 is 100 kHz (kilohertz) and the second frequency F2 is 10 kHz. In another embodiment, the first F1 and second F2 frequencies are 1 MKz and 100 kHz, respectively. In some embodiments, excitation signals 113 are produced in three or more frequencies, denoted F1, F2, F3 . . . Fn. In yet another embodiment a random waveform F∞ contains energies in a wide range of frequencies, enabling the system 100 to generate a graph of the whole spectrum of frequencies across the excitation signals 113.

Excitation signals 113 may further be transmitted with a known phase (e.g. sine or cosine waves). Detection of phase in addition to amplitude by measurement electrodes may further aid the differentiation between working fluid 104 alone, plastic particle, or non-plastic particle. Each frequency of the frequencies F of signals 113 may be further transmitted with different, defined phases.

As one illustrative example, in one case, the upstream electronics 132 are used to supply a voltage to the transmit electrode 111 to produce excitation signals 113 consisting of the superposition of six sinusoids: 215 $mV_{p\text{-}p}$ at 10 kHz, 200 $mV_{p\text{-}p}$ at 90 kHz, 200 $mV_{p\text{-}p}$ at 200 kHz, 200 $mV_{p\text{-}p}$ at 500 kHz, 190 $mV_{p\text{-}p}$ at 1.1 MHz, and 120 $mV_{p\text{-}p}$ at 3 MHz, with zero DC offset. The voltages were selected to avoid amplifier saturation and to have uniform baseline levels. The current passing through the water to the receive electrode 112 is then measured by the downstream electronics 134 (e.g. a transimpedance amplifier).

Circuitry 130

The present invention provides electronic circuits, referred herein as circuitry 130, to provide input current (referred herein as upstream current 133a) to the transmit electrode 111 (enabling the transmission of signals 113) and the reception of the received affected signals 114 from receive electrodes 112. Circuitry 130 is further divided into upstream electronics 132 and downstream electronics 134 for simplicity, however certain components may be grouped into both upstream and downstream. Upstream electronics 132 are connected to the transmit electrode 111 and provide the needed AC potential input (i.e. current input) to generate signals 113. Downstream electronics 134 provide the necessary measurement circuitry to detect at least one of the phase and amplitude of the received signals.

Figure 5A:
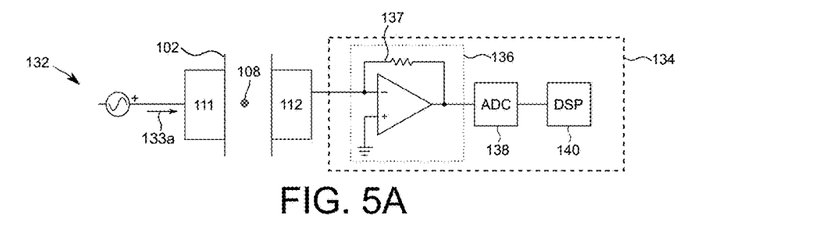
FIGS. 5A-5D, are circuit diagrams of the circuitry according to several embodiments of the present invention.

A basic circuitry 130 outline is illustrated in FIG. 5A, having upstream electronics 132 that connects to at least one transmit electrode 111 and downstream electronics 134 that connect to at least one receive electrode 112. The downstream electronics 134 further includes an amplifier 136, an analog to digital converter (ADC) 138 and a digital signal processor (DSP) 140, or another controller device (e.g. controller 131). Amplifier 136 (most often a transimpedance amplifier) most often consists of an op amp amplifier circuit, enabling a negative feedback, the negative terminal is treated as a virtual ground and the voltage potential coming from the other side of the amplifier is only effective resistance as received from receive electrode 112. Additionally, resistor 137 enables changing the gain of the op amp circuit and can be adjusted to change the resistance to change sensitivity. Additional circuitry 130 layouts are provided in FIGS. 5B-5D for more complex embodiments and described in more detail in the Examples Section below.

In most embodiments, downstream electronics 134 measures at least one of the amplitude or phase of the received signals. Illustrated in FIGS. 4A and 4B are differential signal plots of a plastic particle (FIG. 4A) and an organic particle (FIG. 4B) passing through the system 100 of the embodiment illustrated in FIG. 2A. FIGS. 4A and 4B show the difference of amplitude of signals 113 as a particle 108 passes through detector 110. The differential signal as impedance difference is plotted on the y-axis and time, plotted as recorded sample number is on the x-axis. Differential signal is calculated as the received signal from measurement electrode 112b minus reference electrode 112d. Baseline differential signal 405a and 405b of FIG. 4A, and 455a and 455b of FIG. 4B are seen as the flat section of line 403 and 453, representing working fluid 104 without particles. The first peak 407 in FIG. 4A is an increase in impedance, representing a more resistive environment between transmit electrode 111 and measurement electrode 112b than the environment between transmit electrode 111 and reference electrode 112d. The second peak 409 in FIG. 4A is a decrease in impedance, representing a more resistive environment between transmit electrode 111 and reference electrode 112d than transmit electrode 111 and electrode 112b (i.e. baseline at 112b minus resistive at 112d, resulting in less positive values).

The opposite is true for a non-plastic (e.g. organic) particle when measured with the same embodiment, as illustrated in FIG. 4B. First peak 457 is less resistive and second peak 459 is more resistive. While non-plastic particles are known to be more conductive than plastic particles, the inventive system enables a full reversal of differential signal as seen here, as opposed to simply a decrease in restiveness amplitude between first peaks.

In addition to signals 113 amplitude, circuitry 130 may also detect the phase of a signals 113 with a known phase as it is emitted by transmit electrode 112. Typically, with a working fluid 104 containing no particles, the phase will not be altered (e.g. an emitted sine wave will be received as a sine wave), but a particle may change the phase (e.g. a plastic particle may change an emitted sine wave to a received cosine wave).

Controller 131

Some embodiments of the present invention further include a dedicated controller or other computational device. The controller 131 is connected to the circuitry 130 and is most often configured to receive either downstream current 113b, other output from circuitry 130 or impedance information from the circuitry 130. In most cases, when a controller is present, the controller 131 is configured to instruct circuitry 130 to transmit upstream current 133a and may also instruct the method or type of electrical potential used for in the upstream current 133a.

Figure 7B:
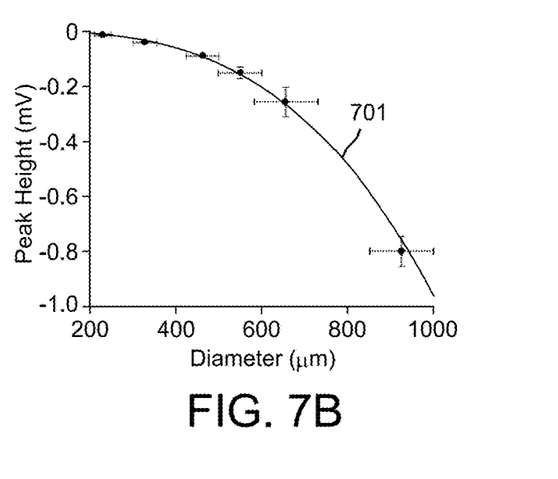

The controller may also be connected to a graphical display unit by a wired or wireless connection. The display enables a user to choose various options for device operation as well as display real-time results of particle detection. In some embodiments, the controller uses the display to plot impendence values of particles passing through the detector. In some cases, the peak height at the first frequency are plotted. And in some cases, the controller displays particles plotted with peak height of the first frequency on one axis and the peak of height of the second frequency on a second axis, as illustrated in FIGS. 7E-G. Peak height comparisons further enable the discrimination of particle types against one another. For example, two peak height comparison readily separates plastic particles (black squares), seed particles (triangles) and organic particles (circles) from one another as illustrated in FIG. 7G.

A graphical display further allows dynamic classification of particles based on one or more parameters measured by the device. For example, a bounding box (or polygon) may be drawn around a region of displayed data as a function of x and y coordinates of a graph (see dotted circle 703 in FIG. 7E). Particles within bounding box 703 are then classified as one type of particle. Particles within additional bounding boxes are classified as additional types of particles. Classification may be done by a user or by automated controller algorithms. Classification can then further enable the device to instruct the operation of additional components, i.e. the movement of a diverter for affecting particle movement through a diverter and to an endpoint (e.g. a clean-up mechanism). These additional components may be connected to either circuitry 130 or controller 131. Automated classification may further adapt as additional particles are measured. For example, an automated bounding area represented as the dashed-dotted oval 705 in FIG. 7E may be automatically adapted into two bounding areas 707 and 709 in FIG. 7G if the circuitry or controller statistically determines that the measured particles are significantly different.

In some embodiments, the detector emits and detects a plurality of frequencies into channel to determine impedance. The circuitry 130 or controller 131 may analyze all of the plurality of frequencies, or a subset of the plurality of frequencies. In some embodiments, the controller further compares several frequencies (typically two) against one another to determine particle parameters. In some cases, the controller compares multiple pairs of frequencies and further determines groupings of particles, typically by bounding box or bounding area. Furthermore, separation of bounding areas for pairs of frequencies can be compared and frequency selection may be performed. Frequency selection may be for only classification (i.e. to reduce the number of frequencies interrogated, limiting computation time and power), or for actual transmission by the transmit electrode. Frequency selection may be done manually by a user or by an automated algorithm.

Calculation of Impedance Change

It is within the scope of the preset invention to calculate the complex impedance change. The magnitude of the complex impedance is defined as the ratio of the voltage amplitude to the current amplitude and the phase of the complex impedance is the phase shift by which the current lags the voltage. The impedance of a two-terminal circuit element is represented as a complex quantity Z. The polar form conveniently captures both magnitude and phase characteristics.

Figure 2C:
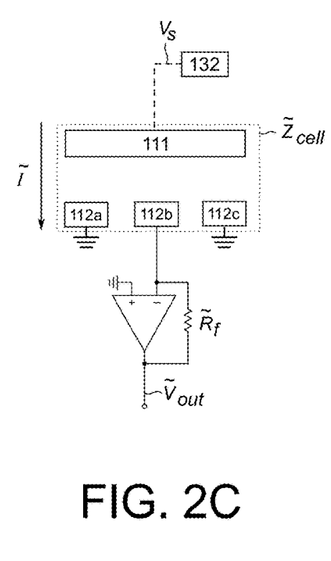

Measurements of the unknown complex impedance (labeled $\tilde{Z}_{cell}$ in FIG. 2C) of the detector (i.e. a flow cell) may be done with the downstream electronics 134 (i.e. a lock-in amplifier and a transimpedance amplifier). A model circuit for describing the impedance measurements conducted is shown in FIG. 2C. Parasitic impedances, such as the inductance of the test leads or stray capacitance, are assumed to be negligible. The circuitry 130, here the transimpedance amplifier (acting in both upstream 132 and downstream 134 electronics) and the lock-in amplifier LIA, are assumed to behave ideally. The lock-in amplifier LIA supplies a sinusoidal source voltage, $V_s$, to the circuit and takes measurements of the output voltage from the transimpedance amplifier, $\tilde{V}_{out}$, by measuring the voltage in phase with the source voltage (i.e. input current), X, and the voltage 90° out of phase, Y. The output voltage can be calculated from measurements of X and Y as shown in Math 3.

$$\tilde{V}_{out}=X+jY \qquad \text{[Math 3]}$$

Where $j=\sqrt{-1}$ is used to denote the imaginary unit. In an ideal transimpedance amplifier 136, the output voltage is related to the input current, $\tilde{I}$, by the feedback resistance, $R_f$ in Math 4.

$$\tilde{V}_{out}=-\tilde{I}R_f \qquad \text{[Math 4]}$$

Since the transimpedance amplifier 136 is assumed to behave ideally, the positive terminal of the transimpedance amplifier acts as a perfect virtual ground. Ohm's law can be used to relate the input voltage to the current and unknown complex impedance as shown in Math 5. And by combining Math 4 and Math 5, the unknown complex impedance is then described in Math 6

$$V_s = \tilde{I}\tilde{Z}_{cell} \qquad \text{[Math 5]}$$

$$\tilde{Z}_{cell} = \frac{-V_s R_f}{\tilde{V}_{out}} \qquad \text{[Math 6]}$$

With particle-free working fluid flow 106, the detector will have an unknown time-varying baseline complex impedance, $\tilde{Z}_{base}$. Particles 108 passing through the detector 110 will change the effective complex impedance between the electrodes, $\Delta\tilde{Z}$. Measurements of the impedance of the detector 110 can then be expressed as in Math 7, and $\Delta\tilde{Z}$ can be broken up into its real (Re) and imaginary (Im) parts, $\Delta$ Re($\tilde{Z}$) and $\Delta$ Im($\tilde{Z}$) as shown in Math 8.

$$\tilde{Z}_{cell}=\tilde{Z}_{base}+\Delta\tilde{Z} \qquad \text{[Math 7]}$$

$$\Delta\tilde{Z}=\Delta\text{Re}(\tilde{Z})+i\Delta\text{Im}(\tilde{Z})=\text{Re}(\tilde{Z}_{cell}-\tilde{Z}_{base})+i \text{ Im}(\tilde{Z}_{cell}-\tilde{Z}_{base}) \qquad \text{[Math 8]}$$

Where measurements of $\tilde{Z}_{cell}$ are continually recorded and $\tilde{Z}_{base}$ is inferred online. Another way of expressing impedance is through its magnitude and phase. The change in the magnitude of the baseline impedance, $\Delta|\tilde{Z}|$, can be written in terms of the magnitude of the detector 110 impedance, $|\tilde{Z}_{cell}|$, and magnitude of the baseline impedance, $|\tilde{Z}_{base}|$ and is shown in Math 9.

$$\Delta|\tilde{Z}|=|\tilde{Z}_{cell}|-|\tilde{Z}_{base}| \qquad \text{[Math 9]}$$

Detection of Impedance Changes

The raw complex impedance data typically consists of a slowly varying baseline signal (i.e. 405a) with sharp peaks corresponding to the change in impedance due to particles 108 passing through the detector 110. First, a controller 131 interprets the data and the time varying baseline impedance is extracted from the raw data using a filter (e.g. a Hampel filter) with a definable sample and time width (e.g. a width of 1000 samples, taking 556 ms) and a threshold of 3 standard deviations for outlier rejection, followed by a moving average filter of a definable sample width (e.g. a width of 101 samples, taking 56 ms). A median filter may be used instead of a Hampel filter. This procedure may be used to identify the baseline real and imaginary impedance as well as the baseline impedance magnitude. The baseline impedance measurements are subtracted from the raw measurements to compute the change in real impedance, $\Delta$ Re($\tilde{Z}$), change in imaginary impedance, $\Delta$ Im($\tilde{Z}$), and change in impedance magnitude $\Delta|\tilde{Z}|$.

Peak and valley locations in $\Delta|\tilde{Z}|$, corresponding to particle detections, may be identified separately using a 'find-peaks' algorithm, with a minimum separation of a definable number of samples (e.g. 150 samples or 83 ms), a minimum amplitude of 3Ω (sigma), along with definable minimum and maximum widths (e.g. a minimum width of 3 samples or 2 ms, and maximum width of 1000 samples or 556 ms). The minimum separation of peaks limits the maximum throughput of the device, as a function of flow 106, for example on the order of 12 detections per second in some cases. Locations may be identified in all frequencies used and then combined, considering any peak location within a definable number of samples of one another to be the same (e.g. 10 samples or 6 ms), to accommodate jitter between the channels.

Clusters of peaks and valleys, closer than the minimum sample separation (e.g. 150 samples), may be assumed to be the result of a singular event and handled heuristically. Three cluster patterns typically occur: (pattern 1) a large amplitude peak next to two small amplitude valleys or vice versa (>6Ω difference), (pattern 2) a large amplitude peak next to one small valley or vice versa (>6Ω difference), (pattern 3) a peak and valley in immediate succession with similar amplitudes (<6Ω difference). The shape of the disturbance due to a particle should be approximately Gaussian, however imperfect baseline subtraction could cause artifacts near peak detections. Patterns 1 and 2 are assumed to be due to a particle passage event with imperfect baseline subtraction, e.g. due to mismatched filter bandwidth, and the largest amplitude peak (or valley) was retained. Pattern 3 is assumed to be the result of imperfect baseline identification during a dynamic baseline change (e.g. when adding water to the channel 102), and both detections were removed. After the peak and valley locations had been found, the maximum amplitude within 10 samples of that location was used for the peak amplitude, again to account for jitter. To remove spurious peaks due to noise, peaks that did not have >3Ω amplitude in at least 2 frequencies were removed. Finally, peaks corresponding to a change in real impedance at a frequency (e.g. 10 kHz>1600Ω) were removed, as they would correspond to a particle 108 larger than what would fit through the 1.7 mm detector 110 in this case.

Figure 9A:
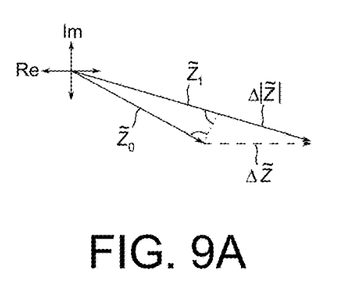
FIGS. 9A and 9B are schematic illustrations of the change in impedance on the complex plane due to a particle. The effect of a plastic particle is illustrated in FIG. 9A and the effect of an organic particle is illustrated in FIG. 9B.
Figure 9B:
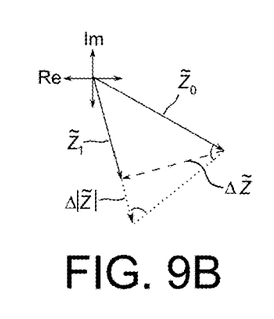

Particle parameters (i.e. plastic vs non plastic) may be determined by using the complex impedance change at one or more frequencies F. By comparing the imaginary and the real components of impedance at one or more frequencies F, particle 108 parameters are readily distinguishable in this system as illustrated in FIGS. 8A-8F. Non-plastic particles have greater magnitude of imaginary impedance than plastic particles (i.e. microplastics), illustrated in FIGS. 9A and 9B. Indeed, at some frequencies (e.g. 1.1 MHz) the direction (positive vs. negative) of complex impedance change is most often in the opposite direction for different particle 108 types (e.g. typically negative for biological particles and typically positive for plastic particles).

Figure 10A:
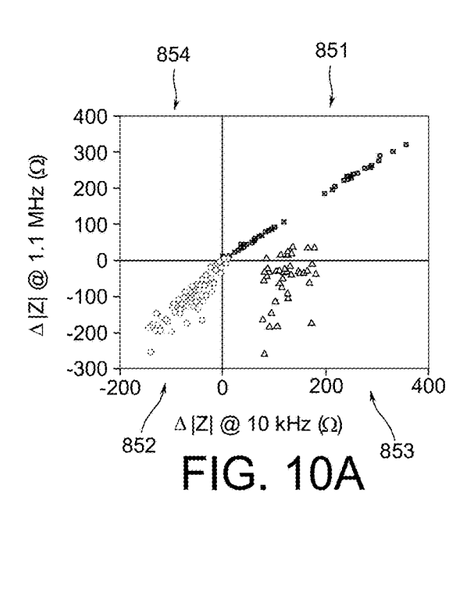

Additionally, particle differentiation may be done by performing a quadrant-based differentiation scheme by comparing measurements of the change in the magnitude of the impedance $\Delta|Z|$ at F1 of 10 kHz vs F2 of 1.1 MHz (FIG. 10A). Particles within quadrant 851, which is positive for both F1 and F2 were plastic particles (black squares), while biological particles (while circles) clustered in quadrant 852, which is negative for both F1 and F2. Additional types of biological particles (seeds, white triangles) clustered in different quadrants, specifically quadrant 853, which is positive for F1 and negative for F2. While quadrant 854 is empty of all particles, in this case.

Figure 10B:
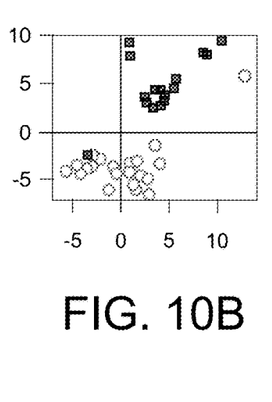

Using a quadrant-based scheme, one small-amplitude microplastic particle detection would be misclassified as an organism and two small-amplitude biological detections would be misclassified as plastic, for the same false positive rate as the 12-D kNN, illustrated in FIG. 10B. Simple logic-scheme may be implemented on low-cost microcontrollers, enabling real-time microplastic sorting.

Particle Classification

It is within the scope of the preset invention to classify detected particles 108. Classification enables the differentiation of particles into groups, for example, into plastic, biological material, bubble groupings, and the like. The system and method of classification may be any suitable classification as known in the art. In one embodiment, the particle classification is done by using k-nearest neighbors (kNN). One possible classification scheme will now be described, comparing two weighted kNN classifiers: a 12-dimensional (12-D) kNN, trained using the change in real and imaginary impedance of all frequencies Fn used (in this example 6 frequencies), and a 2-D kNN, trained using the change in the magnitude of the impedance at a first, low frequency F1 of 10 kHz and a second, high frequency F2 of 1.1 MHz.

The 2-D kNN was used to evaluate if fewer parameters could be measured in additional iterations. Both kNNs were trained using the detections in the interquartile range for each experiment, using the MATLAB Classification Learner App and 10-fold cross-validation. The interquartile range was determined using a measurement proportional to the ESD of the detected particle 108, the cube root of the change in real impedance at 10 kHz. All detections were then classified using the trained models, and the true positive rate for detecting microplastics, false positive rate due to biology misclassification, and false positive rate due to bubble misclassification.

Additional classification may include outlier removal. Impedance changes, due to disturbances such as entrained bubbles, vibration, electrical noise, imperfect baseline identification, or microfiber contamination, can appear as extra detections. To ensure all detections with the system 100 were due to microplastic particles, and not disturbances, an outlier detection algorithm may be used to find detections with anomalous size, based on the ESD, for each experiment run. The outliers were assumed to be due to disturbances and analyzed separately. All other detections were assumed to be true detections of microplastic particles and used to evaluate the true positive rate of the two kNN classifiers. The recovery rate is the number of true microplastic detections divided by the total number of microplastics used in a test experiment (e.g. n=20), expressed as a percent.

Identification System 162

In some embodiments of the present invention, system 100 determines if a particle is plastic or a non-plastic, while a second, interconnected identification system 162 determines the exact type of plastic a particle comprises. Inclusion of an identification system 162 is optional and would not affect the determination of a particles 108 nature (i.e. plastic or organic). The identification system 162 may be any suitable sensing mechanism as known in the art. In one embodiment, identification system 162 comprises an attenuated total reflectance Fourier-transform infrared spectroscopy (ATR-FTIR) system, enabling 99% correct identification of plastic particles. In another embodiment, identification system 162 comprises a near-IR reflectance spectroscopy system, enabling approximately 90% correct identification of plastic particles. In yet another embodiment, identification system 162 comprises a laser induced breakdown spectroscopy (LIBS) system, enabling approximately 97% correct identification of plastic particles. In yet another embodiment, identification system 162 comprises a mid-IR spectroscopy system.

In some embodiments, a clean-up mechanism 164 is included downstream of system 100 or identification system 162, if included. The clean-up mechanism 164 enables plastic particles to be removed from the working fluid 104 before that liquid is placed back into the environment. In these embodiments, the clean-up mechanism 164 may be programmed or directed to remove only certain types of plastic particles. In some cases, a clean-up mechanism 164 is included in embodiments without an identification system 162. In these cases, all non-organic particles would be diverted to the clean-up mechanism 164.

Diverter 166

Additional components (e.g. identification system 162) are connected to system 100 via a suitable connection mechanism 160. Typically, the connection mechanism 160 is the same or similar to channel 102 and preferably is able to convey suspended particles 108 in working fluid 104 to the additional component without alteration, or without unknown alterations.

In some embodiments, identification system 162 is further connected to system 100 via a diverter mechanism 166. Diverter 166 comprises a suitable mechanism enabling changing liquid flow to one of a plurality of end points. In one embodiment, diverter 166 comprises a common valve connected to the circuitry 130. Circuitry 130 instructs the valve 166 to direct flow to one or more of the following group of identification system 162, an organic particle collector, clean-up mechanism 164, a waste stream, or the like. The diverter may be connected to the channel 102, the connection mechanism 160, at the junction of the two, or at another suitable location (i.e. after the identification system 162).

Figure 6A:
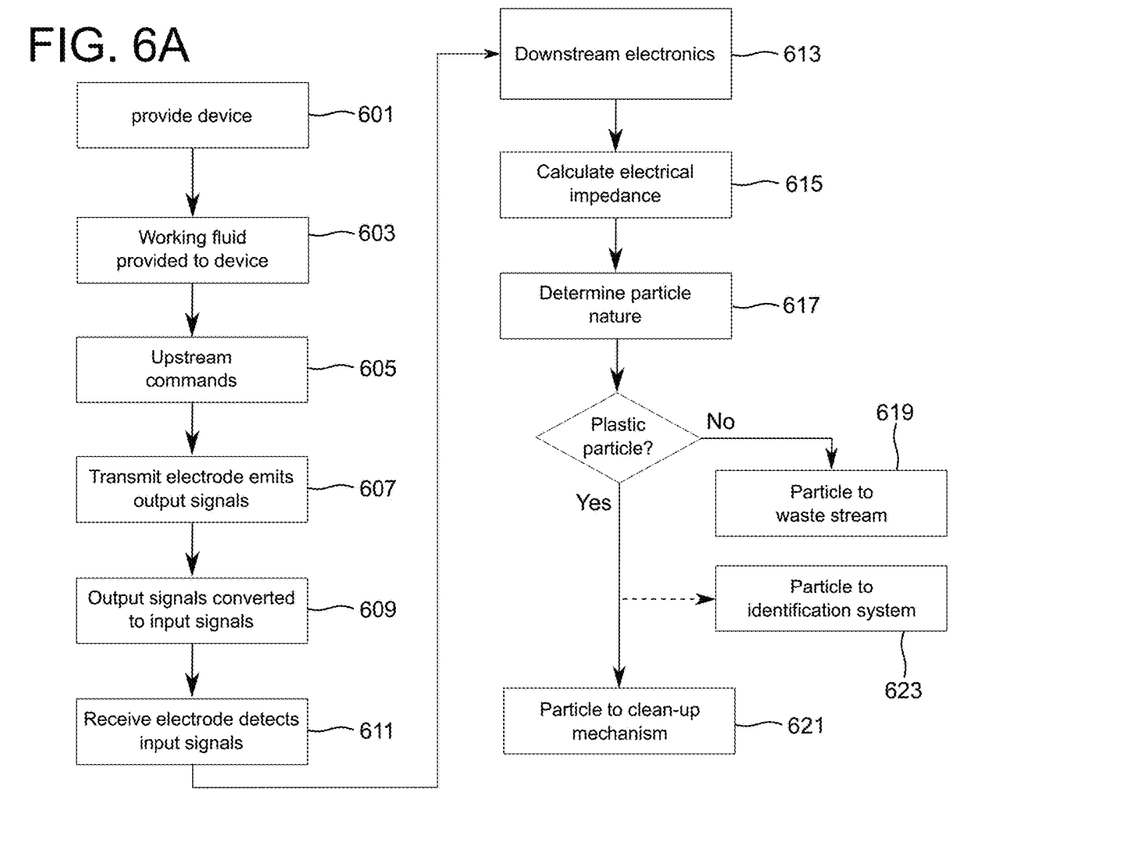
FIGS. 6A and 6B are schematic flow diagrams illustrating the method of operation of two embodiments of the present invention.
Figure 6B:
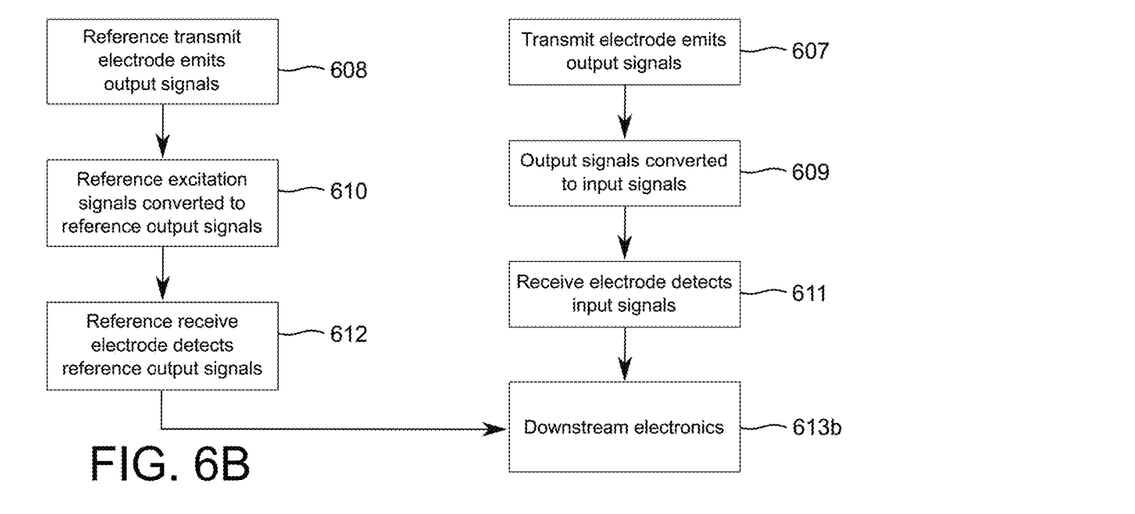

In one embodiment, the circuitry 130 determines if a particle's nature (step 617 in FIG. 6A). If the particle is not plastic (i.e. organic), it is diverted to a waste stream (step 619), for example back into an aquatic environment. If the particle is plastic, the particle is diverted to a clean-up mechanism 164 (step 621). In another embodiment, if the particle is plastic, it is diverted to an identification system 162 for further analysis (step 623). Both preceding embodiments are depicted in FIG. 6A by the solid and dashed lines leading to steps 621 and 623, respectively.

Examples

Several aspects of the present invention will now be discussed in relation to several specific examples, each example illustrated, in turn, in FIGS. 5A-5D. A first example is illustrated in FIG. 5A and its method of use is diagrammed in FIG. 6A. First, a device is provided that has at least the components shown in FIGS. 1 and 2A (and shown as a method of use in FIG. 6A's step 601). Next, a working fluid 104 is introduced into channel 102 (step 603 in FIG. 6A), this may be accomplished by any means as known in the art, most often by either connecting to an existing water line, pipe, or by supplying the working fluid 104 into a bottled channel 102. Current input (i.e. upstream current, depicted as arrow 133a) is sent to the transmit electrode 111 (step 605) by either circuitry 130 or a microcontroller 131, if present. The commands could be digitally generated (e.g. from microcontroller or field programmable gate array, FPGA) or generated via analog electronics (e.g. a sine wave oscillator). Then the transmit electrode 111 emits excitation signals 113 into the working fluid 104 (step 607). Appropriate buffer electronics depend on the method of generating the excitation signals 113 from upstream current 133a, would be commonly known and are not illustrated in FIG. 5A. The excitation signals 113 could be a simple sine wave, a sum of sine waves, an arbitrary repetitive waveform like a ramp or square wave, a coded sequence, or a pseudorandom waveform as would be used for stochastic system identification. The excitation signals 113 are converted to affected signals 114 by the electrical properties of the working fluid 104 and any suspended particles 108 therein (step 609).

The transmit electrode 111 is in electrical contact with the working fluid 104 in the flow channel 102. Working fluid in the flow channel 102 could be a wide range of conductivities or types (e.g. saltwater, fresh water, phosphate-buffered saline, and the like). The receive electrode 112 is in electrical contact with the fluid in the flow channel 102 as well. A particle 108 is shown in the channel 102. The receive electrode continuously detects the affected signals 114 that have traveled through the channel 102 and working fluid 104 (step 611 in FIG. 6A) and the receive electrode 112 generates downstream current 133b. The downstream electronics 134 then continually receives the downstream current 133b (step 613) and determines the electrical impedance between the transmit 111 and receive 112 electrodes (step 615). Impedance may be inferred from comparing known excitation signals 113 to the affected signals 114. Different parts of the impedance spectrum are probed based on the frequency content of the excitation 113 and affected signals 114.

In this example, an amplifier 142 (most often a differential amplifier) converts the current passing from the transmit 111 to the receive 112 electrodes (i.e. affected signals 114) into a voltage scaled by the feedback resistor 137, thereby amplifying the difference between two receive electrodes (e.g. 112b and 112d) and the output from the amplifier is only the difference (a delta) between the two receive electrodes, thus improving sensitive and signal to noise. The current passing through the flow channel 102 is related to the impedance of the channel via Ohm's law (also see Equation 1): V=I Z, where Z is the complex impedance of the flow channel 102, I is the current, and V is the voltage across the channel. The negative input of the amplifier 142 acts as a "virtual ground" allowing us to treat the voltage across the channel as the same as the output signal voltage. The positive input to the op amp is held at a fixed bias. Here it is shown as ground, but if single supply operation is desired a different bias, for example half the supply voltage, can be used. If this is used, the output signal will also be at the same bias, so that no DC signal is present between the transmit and receive electrodes.

An analog to digital converter (ADC) 138 with appropriate anti-alias circuitry converts the received voltage signal into a digital signal. Digital signal processing (DSP) is performed on the data. This may be done on a dedicated digital signal processor chip 140, on a microcontroller, on an FPGA, or on a computer, and the like. The processing compares the excitation signals 113 to the affected signals 114 or the converted digital signal to compute the amplitude and phase difference. For example, if a waveform consisting of the sum of two sine waves of different frequencies is the excitation signal, the digital signal processing could consist of performing an FFT on the digital signal data output by the ADC 138 and obtaining the magnitude and phase of the received waveform at those two frequencies, and then calculation of the impedance at those two frequencies via Ohm's law. It would improve the measurement to also monitor the output signal via another ADC. Further improvement can be made by using a phase locked loop in the case of stochastic system identification, or digital or analog lock-in amplification, for output signals with sums of pure sine waves.

Once the circuitry 130 has received the downstream current 133b, it is enabled to determine the impedance between transmit and receive electrodes. When a particle 108 passes the electrodes, the impedance changes (see FIGS. 4A and 4B), and the circuitry (or a controller if present) can determine if a particle is a plastic particle or organic particle, in other words, determine the particle's nature (step 617 in FIG. 6A).

Figure 5B:
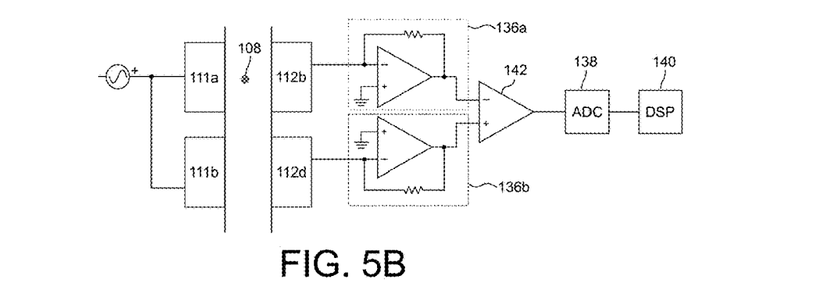

A second example is illustrated in FIG. 5B, this embodiment essentially has two times the electrode-transimpedance amplifier circuits as are used above, in FIG. 5A. The voltage at the output of the two transimpedance amplifiers 136a and 136b is proportional to the impedance of the electrical path between the electrodes. Here the upper electrode set (transmit 111a and receive 112b) has a particle 108 between it and the lower electrode set (transmit 111b and receive 112d) has just fluid 104. Many different configurations of the transmit and receive electrodes are possible, including the use of a single transmit electrode 111 (rather than 2 as illustrated in FIG. 5B) or the use of guard electrodes that ensure uniform electric field, reject noise, or otherwise alter the electrode configuration. The core concept here is a circuit that outputs a signal proportional to the difference in impedance between the two electrical paths (excitation signals 113a and 113b, not illustrated). This allows fluids of changing conductivities to be used and, since amplification can be added, allows pickup of much smaller signal changes, which enables lowering the detection limit to even smaller particles.

An instrumentation amplifier 142 is used to amplify the difference in impedance between the two fluid paths. Appropriate compensation electronics to adjust for minor discrepancies in electrode configuration impedance are not shown. An example correction might be a DC offset correction for a slight difference in the impedance of the electrical path to the electrodes, or differences in the electrodes themselves (e.g. area, electrode fouling, parasitic inductance/capacitance/resistances). The output of the instrumentation amplifier 142 is proportional to the impedance difference between the two electrode sets, so it can be directly related the effect of the particle's presence. Amplification allows detection of smaller particles, but in principle unity gain (or even fractional gain) could be used, depending on the input range of the analog to digital converter 138.

Again, the received voltage signal is converted into a digital signal by an ADC 138 and digital signal processing is again used to infer the particle's character (i.e. parameters). Here the process is made slightly simpler, as the signal is related directly to the particle's impact, whereas in the first example (FIG. 5A) a comparison between signal with a particle and signal without a particle must be made. This embodiment outputs the characteristic 2 peak signals with a peak then a valley, as illustrated in FIGS. 5A and 5B. The peak height can be related to the impedance of the particle 108, and a benefit of this measurement is the resulting two measurements at once (peak height and valley depth), which can be used to reduce uncertainty. The time between the peak and valley is a measure of flow rate, thereby enabling this sensor to also detect flow rate.

Figure 5C:
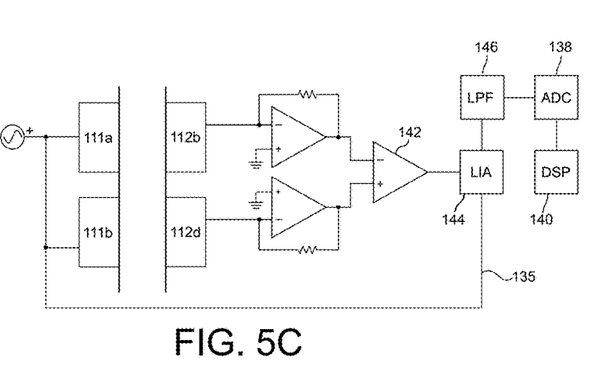

A third example is illustrated in FIG. 5C, representing the same circuit as above in the second example, but elaborates on how lock in amplification can be done. A lock in amplifier (LIA) 144 performs very precise amplification at a single frequency and allows the amplitude and phase difference to be known quite well. Separate lock-ins would be needed for multiple frequencies. FIG. 5C illustrates a simple block for the LIA 144, but as commonly known, it often consists of a few electrical components. In the analog domain, the lock in amplifier 144 multiplies the signal received from the instrumentation amplifier 142 by the signal output to the transmit electrodes 111*a* and 111*b*. It does this twice, once with an in-phase signal and once with a 90 degree phase shifted signal. This allows for the circuit to obtain amplitude and phase information. The signal output from the multiplier essentially creates two copies of the impedance signal, one copy at DC and one copy at twice the modulation frequency. A low pass filter (LPF) 146 is used to obtain just the DC copy. The DC-located copy of the signal is digitized and then processed via digital signal processing.

Figure 5D:
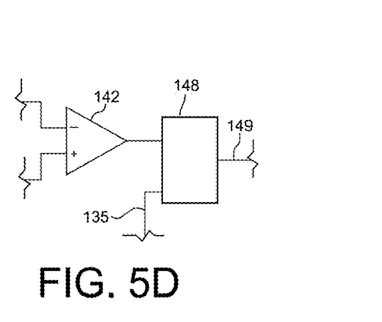

A fourth example is illustrated in FIG. 5D, with a digital lock-in amplification method. All analog lock in processes (e.g. the signal multiplication, the low pass, and the phase locked loop), can be done digitally. Modern FPGAs can now do this incredibly fast and with accuracies that exceed that of analog circuitry. Lock in amplifiers (digital or analog) 148 may be either custom built or purchased (e.g. the HF2LK from Zurich Instruments). Digital processing can be included in the FPGA coding algorithm, so the output of this signal block could be a complex impedance difference between electrode sets (e.g. set 111*a* and 112*b* and set 11*b* and 112*d* in FIG. 5C). Output signal 135 from the upstream electronics 132 is combined with the output from the amplifier 142 to the digital lock in 148 and produces a digital output 149. The digital output 149 may then be read for impedance magnitude and phase. An alternative to the examples above combines the analog to digital converter 138 after amplifier 142 (i.e. an embodiment with LIA 144 or LPF 146). The analog to digital converter 138 then connects into an amplifier 148, either a digital amplifier or an analog amplifier. The output of the amplifier 148 is then used for impedance magnitude, phase, or both magnitude and phase.

A fifth example is illustrated in FIG. 7A having a channel 102 bringing particles 108 past a flow cell (i.e. detector 110) and circuitry 130 connected to the flow cell. Circuitry 130 comprised of a lock-in amplifier connected to (i) the transmit electrode and (ii) a 2 channel transimpedance amplifier. The amplifier is also connected to receive electrodes 112*b* and 112*d*. Guard electrodes 112*a*, 112*c* and 112*e* are connected to ground.

Potable tap water filtered to 53 micrometers (m) was used as working fluid. Test particles were suspended in the working fluid, including polyethylene plastic beads of 6 sizes, ranging from 212 to 1000 m. Samples of 20 plastic particles from each size range were used to quantify detection rates. Non-plastic particles were volvox globator (about 200 to 400 µm), moina (about 300 to 800 µm), brine shrimp eggs, brine shrimp nauplii (less than 400 µm), teff (about 600 µm), and poppy seeds (about 800 µm). FIG. 7B illustrates the impedance peak height in millivolts as a function of particle diameter in micrometers. The Coulter Principle states that the impedance change of the working fluid as a particle passes through the detector 110 is a function of the volume of that particle 108. A cubic polynomial (line 701) is fit to the peak height as a function of particle diameter using total least squares under the constraint that a zero diameter particle should be zero peak height. Vertical error bars represent the 1 sigma deviation of peak height data and horizontal error bar represent the size range from the particle provider.

Figure 7C:
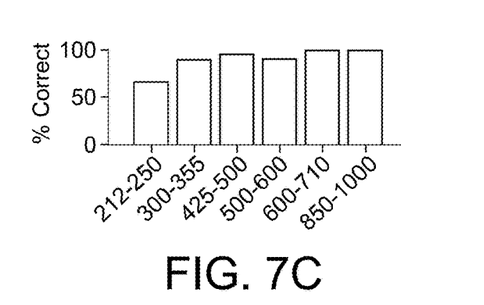
Figure 7D:
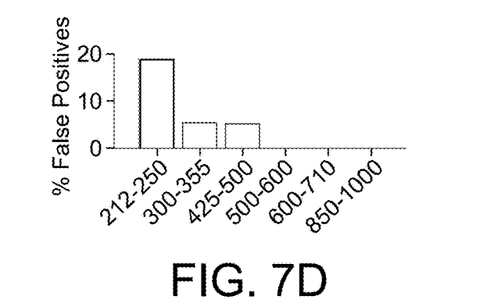
Figure 7E:
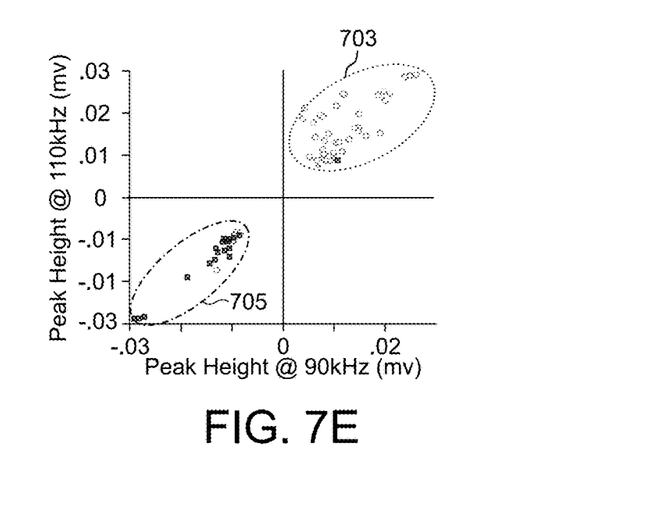
Figure 7F:
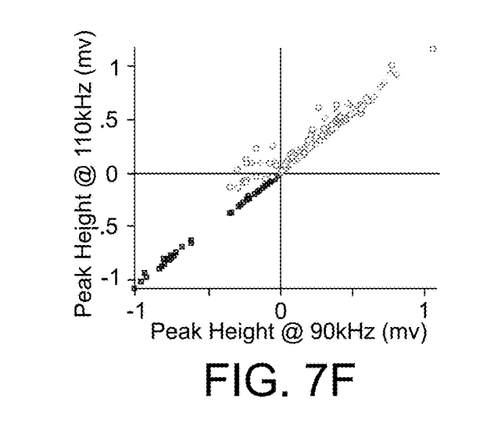
Figure 7G:
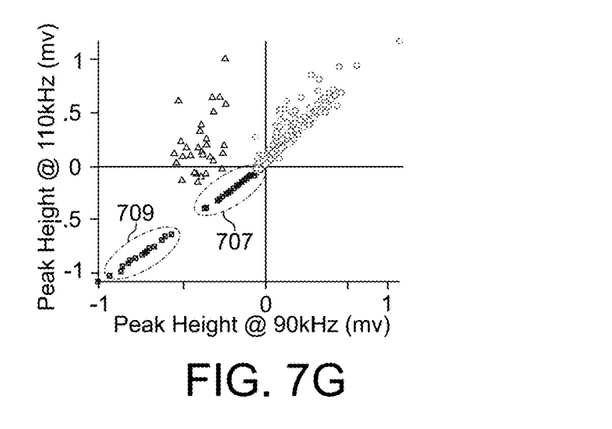
Figure 8A:
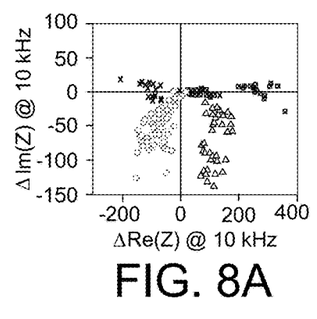
FIGS. 8A-8F illustrate the real and imaginary impedance change at six frequencies analyzed for many particles in one embodiment.
Figure 8B:
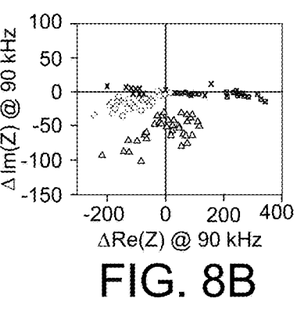
Figure 8C:
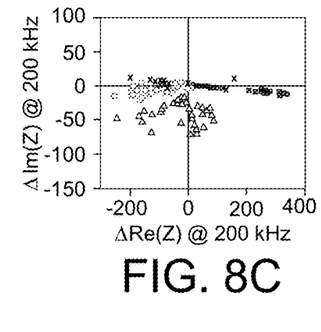
Figure 8D:
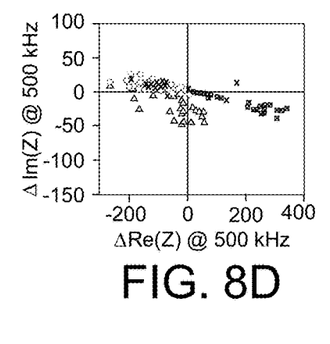
Figure 8E:
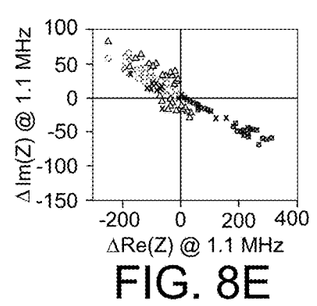
Figure 8F:
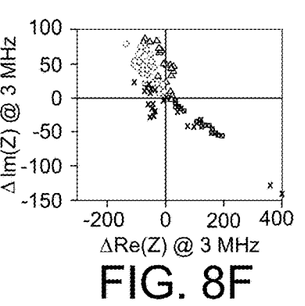

This exemplary embodiment was run with twenty plastic particles in each size range, illustrated in FIG. 7C. The particle size relationship to peak height was used to identify detected size. Good performance is observed for larger particles, see FIGS. 7C and 7D (x axis is size of particles in µm). From these results, detection limit of the prototype device is around 200 µm. Detected particles of the incorrect size for the experiment are treated as false positives, however they could be due to contamination (e.g. clothing fibers). Next, plastic (squares) and biological (circles) samples were tested on this exemplary embodiment. Samples of different compositions were well differentiated using measurements of the impedance change using a first frequency F1 of 90 kHz and a second frequency F2 of 1.1 MHz and comparing peak height at 90 F1 (kHz) and F2 (1.1 MHz), illustrated in FIGS. 7E-7G. Peaks were primarily positive in both frequencies for biological samples (graphed as highest peak point relative to baseline) and negative in both frequencies for plastic. Of the 779 particles detected, one plastic particle is misidentified as biological and 8 biological samples were misidentified as plastic. All were in the size range about 200 µm and could be a result of contamination. Additionally, different biological types could be differentiated using the peak height signal at a frequency of 10 kHz.

Although specific features of the present invention are shown in some drawings and not in others, this is for convenience only, as each feature may be combined with any or all of the other features in accordance with the invention. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A device for the measurement of impedance properties of particles
   suspended in a liquid,
   comprising:
   a channel comprising a first and second wall, said channel configured to constrain a working fluid;
   a transmit electrode in contact with said first wall;
   a first receive electrode in contact with said second wall;
   circuitry connected to said transmit electrode and said first receive electrode; wherein said circuitry is configured to supply upstream current to said transmit electrode; wherein said transmit electrode is configured to emit excitation signals having at least one frequency into said channel and said first receive electrode is configured to receive said excitation signals, producing first downstream current; and wherein said circuitry measures impedance of said working fluid using said first downstream current and determines (i) the presence of a suspended particle in said working fluid and (ii) at least one parameter of said suspended particle;

a second receive electrode connected to said circuitry, in contact with said second wall, and positioned opposite said transmit electrode; wherein said second receive electrode is configured to receive said excitation signals, producing second downstream current and wherein said circuitry measures impedance of said working fluid using said second downstream current; and a first guard electrode having a fixed potential connected to said circuitry, in contact with said second wall, and positioned opposite said transmit electrode; wherein said first guard electrode is configured to receive said excitation signals.

2. The device of claim 1 wherein said at least one parameter is said suspended particle's composition of either (i) plastic substance or (ii) organic material.

3. The device of claim 1 further comprising:
a second and a third guard electrode having fixed potentials connected to said circuitry, in contact with said second wall, and positioned opposite said transmit electrode;
wherein said second and third guard electrodes are configured to receive said excitation signals, producing fourth and fifth downstream current, respectively;
wherein said circuitry measures said fourth and fifth downstream current; and
wherein said first guard electrode is positioned in front of said first receive electrode,
said second guard electrode is positioned between said first and second receive electrodes, and said third guard electrode is positioned behind said second receive electrode.

4. The device of claim 1 further comprising a controller connected to said circuitry and said controller is configured to receive information on said impedance of said working fluid and determine at least one parameter of said particle by calculating the complex impedance change.

5. The device of claim 4 wherein said controller determines said at least one parameter of said particle by further comparing the imaginary and real components of said complex impedance change.

6. The device of claim 1 further comprising a reference mechanism comprising:
a reference container constraining a reference liquid;
a reference transmit electrode connected to said circuitry, in contact with said reference liquid, and configured to emit reference excitation signals having at least one frequency into said reference container; and
a first reference receive electrode in contact with said reference liquid and positioned opposite said transmit electrode;
wherein said first reference receive electrode is configured to receive said reference excitation signals, producing reference downstream current; and
wherein said circuitry measures said reference downstream current.

7. The device of claim 1, wherein said working fluid moves through the length of said channel.

8. A method for the measurement of impedance properties of particles suspended in a liquid, comprising the steps of:

(a) selecting a device comprising:
a channel having a wall configured to constrain a liquid;
a transmit electrode in contact with said channel;
a first receive electrode in contact with said channel and positioned on a wall opposite said transmit electrode;
circuitry connected to said transmit electrode and said first receive electrode; a second receive electrode connected to said circuitry, in contact with said second wall, and positioned opposite said transmit electrode, wherein said second receive electrode is configured to receive said excitation signals, producing second downstream current and a first guard electrode having a fixed potential connected to said circuitry, in contact with said second wall, and positioned opposite said transmit electrode, wherein said first guard electrode is configured to receive said excitation signals;

(b) supplying a working fluid comprising suspended particles to said device;
(c) emitting, from the transmit electrode, excitation signals into said working fluid;
(d) receiving said excitation signals with the said first electrode, producing first downstream current;
(e) measuring at least one of resistance and capacitance of a particle wherein said particle is suspended between said transmit electrode and said first electrode;
(f) sending first downstream current to said circuitry;
(g) determining impedance of said working fluid with said circuitry and utilizing said first downstream current; and
(h) determining at least one parameter of said particle using said impedance of said working fluid and utilizing said second downstream current.

9. The method of claim 8 wherein said at least one parameter is said suspended particle's composition of either (1) plastic substance or (2) organic material.

10. The method of claim 8 wherein said at least one parameter is said suspended particle's composition of either (1) plastic polymers or (2) organic material.

11. The method of claim 9 further including the steps of:
(i) connecting a diverter to said device, said diverter leading to at least a clean-up mechanism; and
(j) diverting particles having compositions of plastic polymers to said clean-up mechanism.

12. The method of claim 9 further including the steps of:
(k) connecting an identification system to said device; and
(l) identifying the type of plastic type of particles having compositions of plastic polymers to said clean-up mechanism.

13. The method of claim 9 further including the steps of:
(m) connecting a diverter to said device, said diverter leading to at least an identification system;
(n) diverting particles having compositions of plastic polymers to said identification system; and
(o) identifying the type of plastic of said diverted particles.

14. The method of claim 8 wherein said device further comprises:
a second and a third guard electrode having fixed potentials connected to said circuitry, in contact with said second wall, and positioned opposite said transmit electrode;
wherein said second and third guard electrodes are configured to receive said excitation signals; and
wherein said first guard electrode is positioned in front of said first receive electrode, said second guard electrode is positioned between said first and second receive electrodes, and said third guard electrode is positioned behind said second receive electrode.

15. The method of claim 8 further including the step of (p) connecting said device to a controller, said controller configured to receive information on said impedance of said working fluid and determine at least one parameter of said particle by calculating the complex impedance change.

\* \* \* \* \*